United States Patent [19]

Calderale et al.

[11] Patent Number: 5,127,914
[45] Date of Patent: Jul. 7, 1992

[54] OSTEOSYNTHESIS MEANS FOR THE CONNECTION OF BONE FRACTURE SEGMENTS

[76] Inventors: Pasquale M. Calderale, Via Comissetti, 11, Pianezza, Italy, 10044; Francesco Pipino, Via Torre di Brengola, 4/6, Palese-Bari, Italy, 70057

[21] Appl. No.: 478,301

[22] Filed: Feb. 9, 1990

[30] Foreign Application Priority Data

Feb. 10, 1989 [IT] Italy ................................ 67072 A/89

[51] Int. Cl.⁵ ........................ A61B 17/56; A61B 17/58
[52] U.S. Cl. ........................ 606/65; 606/66; 606/71
[58] Field of Search ................. 606/60, 65, 66, 69–71

[56] References Cited

U.S. PATENT DOCUMENTS 3,554,193  1/1971  Konstantinou et al. ............ 606/65
3,842,825 10/1974  Wagner ............................... 606/66
4,388,921  6/1983  Sutter et al. ........................ 606/71

FOREIGN PATENT DOCUMENTS 0355035  2/1990  European Pat. Off. .
3027148 12/1981  Fed. Rep. of Germany .
2254298  7/1975  France .
2499400  8/1982  France .
8904150  5/1989  PCT Int'l Appl. .

Primary Examiner—Ronald Frinks
Attorney, Agent, or Firm—Klauber & Jackson

[57] ABSTRACT

Osteosynthesis means comprising a plate secured to one bone fracture segment, and at least a screw inserted inside a hole on the plate and screwed into corresponding holes in the bone segments; characterized by the fact that they comprise an angle joint located between the screw and the hole in the plate, and designed to enable the axis of the screw to be positioned in relation to the plate at any angle within a conical surface whose axis coincides with that of the hole in the plate.

12 Claims, 3 Drawing Sheets

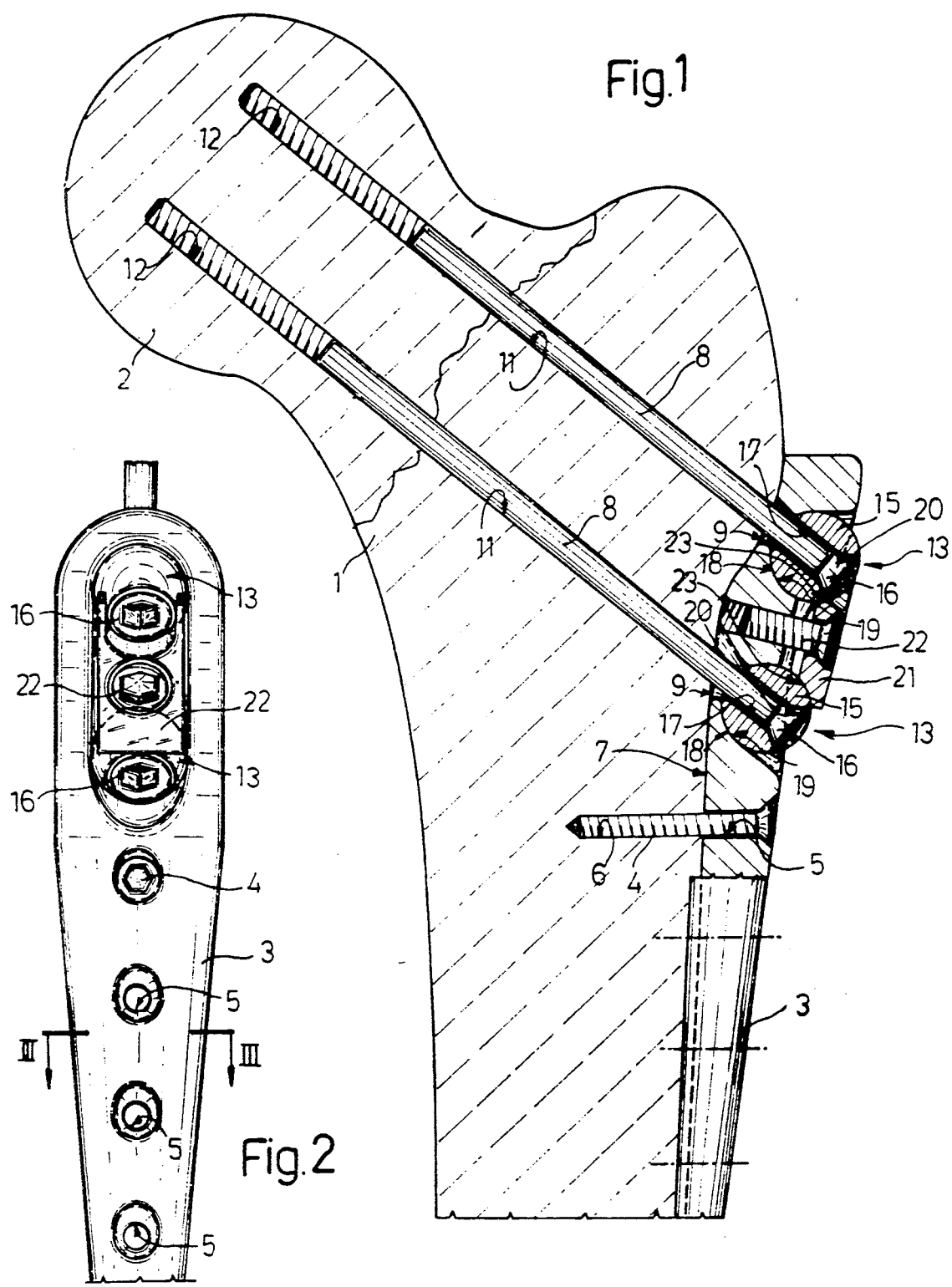

OSTEOSYNTHESIS MEANS FOR THE CONNECTION OF BONE FRACTURE SEGMENTS

BACKGROUND OF THE INVENTION

The present invention relates to osteosynthesis means for the treatment of bone fractures and in particular for the connection of bone fracture segments.

The assemblies currently employed for the treatment of bone fractures substantially comprise a plate secured surgically to one of the bone fracture segments, e.g. by means of one or more screws inserted through holes on the plate and screwed into matching holes on the bone segment; and at least one screw inserted through a further hole on the plate and screwed into a matching hole on both segments. Once the bone segments are firmly knit, the various elements in the assembly are removed. Said second screws inserted inside the second segment for connecting it to the first are longer than those connecting the plate to the first segment, and must be positioned at a predetermined angle in relation to the plate, so as to fit precisely inside the matching holes on the second segment.

Assemblies of the type briefly described above present a number of drawbacks.

Firstly, they fail to provide for correct support between the plate and mating segment when the screws connecting the two segments are screwed inside the respective holes on the same. This is due to the axes of said screws forming a predetermined angle in relation to the plate, which permits no or only a very small amount of adjustment, i.e. that permitted by the slack between the hole in the plate and the screw shank. Very rarely, however, does said angle correspond to that formed between the axes of the holes in the bone segments and the plate supporting surface on the bone.

Secondly, assembly of the various component parts involved to the bone segments is not only difficult but requires considerable care and skill.

Thirdly, the versatility of assemblies of the aforementioned type is extremely limited, by virtue of the size and shape of the component parts depending on the geometrical characteristics of the bone segments for connection.

Fourthly, known assemblies of the aforementioned type may lead to complications and delayed healing of the fracture in the period immediately following the surgical operation. During this period, in fact, absorption generally takes place at the fracture surfaces, thus altering the position of the ends of the bone segments, which, using known assemblies of the aforementioned type, are prevented from moving by the rigid restraints consisting of the plate and respective screws. This results in undue stress on the fracture surfaces, which may even be caused to move away from each other.

Finally, the mechanical strength and stability of the connection provided for by such assemblies are fairly poor, so that steps must be taken for preventing relative movement of the bone segments in the period immediately following surgery.

SUMMARY OF THE INVENTION

The aim of the present invention is to provide osteosynthesis means for the connection of bone fracture segments of the type briefly described above, and designed to overcome the aforementioned drawbacks, i.e. means enabling highly accurate positioning and strong, reliable connection of the bone segments; fast, easy assembly; maximum versatility in terms of application; and rapid healing of the bone fracture.

With these aims in view, according to the present invention, there are provided osteosynthesis means for the connection of bone fracture segments, comprising a plate secured to one of said segments; and at least a screw inserted inside a hole on said plate and screwed into corresponding holes in said segments; characterised by the fact that they also comprise an angle joint located between said screw and said hole in said plate, and designed to enable the axis of said screw to be positioned in relation to said plate at any angle within a conical surface whose axis coincides with that of said hole in said plate.

BRIEF DESCRIPTION OF THE DRAWINGS

The present invention will be described in detail, by way of a non-limiting example, with reference to the accompanying drawings, in which:

FIG. 1 shows a partially-sectioned side view of a first embodiment of the means according to the present invention, employed for connecting two femur segments;

FIG. 2 shows a plan view of the FIG. 1 means;

DETAILED DESCRIPTION OF THE INVENTION

Figure 6:
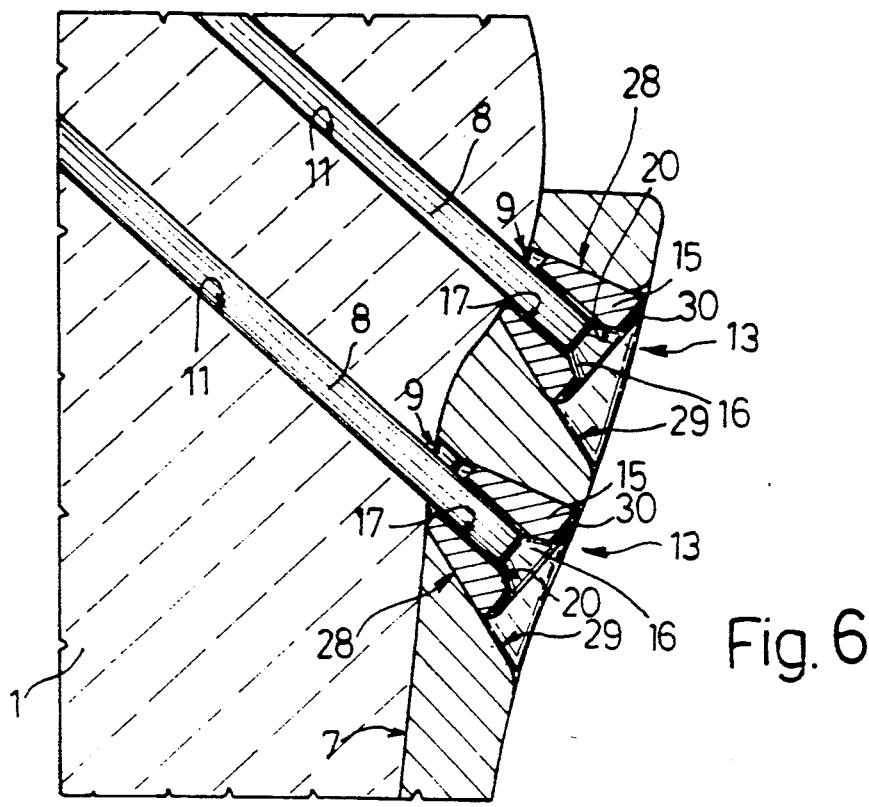
FIG. 6 shows a section of part of a further embodiment of the means according to the present invention.

As shown in FIG. 1, the means according to the present invention provide for connecting two bone fracture segments, e.g. femur segments 1 and 2, and substantially comprise a plate 3 secured in any convenient manner to one of said segments, e.g. segment 1, using screws 4 inserted inside holes 5 on plate 3 and screwed into corresponding holes 6 in segment 1. Surface 7 of plate 3 contacting the surface of segment 1 is conveniently designed to rest directly on said segment surface.

The means according to the present invention also comprise further screws 8, each designed to fit through a hole 9 on the end portion of plate 3, through a hole 11 in segment 1, and to screw into a hole 12 in segment 2. As shown in FIG. 1, only end portion 27 of each screw 8 is threaded, whereas the rest of the shank is smooth, and each threaded portion 27 is shorter than the respective hole 12 in segment 2.

The means according to the present invention also comprise an angle joint 13 located between each screw 8 and respective hole 9 in plate 3, and designed to enable the axis of screw 8 to be positioned in relation to plate 3 at any angle within a conical surface the axis of which coincides with that of hole 9.

Each angle joint 13 may conveniently be designed as shown in FIGS. 1 and 2, in which case, it comprises an adjustable element 15 housing head 16 of screw 8, and having a hole 17 for the shank of the same. Each adjustable element 15 also comprises at least a spherical surface portion 18 designed to mate with a spherical seat 19 formed about hole 9 on plate 3, and conveniently consists simply of a ball with a hole 17, as shown in the FIG. 1 embodiment.

Each adjustable element 15 also presents a seat 20 housing head 16 of screw 8.

Means are provided for locking angle joints 13 and securing screw 8 at a predetermined angle in relation to plate 3, said means conveniently comprising a plate 21 secured to plate 3 by means of at least a threaded connecting member 22, and having surface portions 23 designed to exert predetermined pressure on adjustable element 15 for preventing movement of the same.

Figure 4:
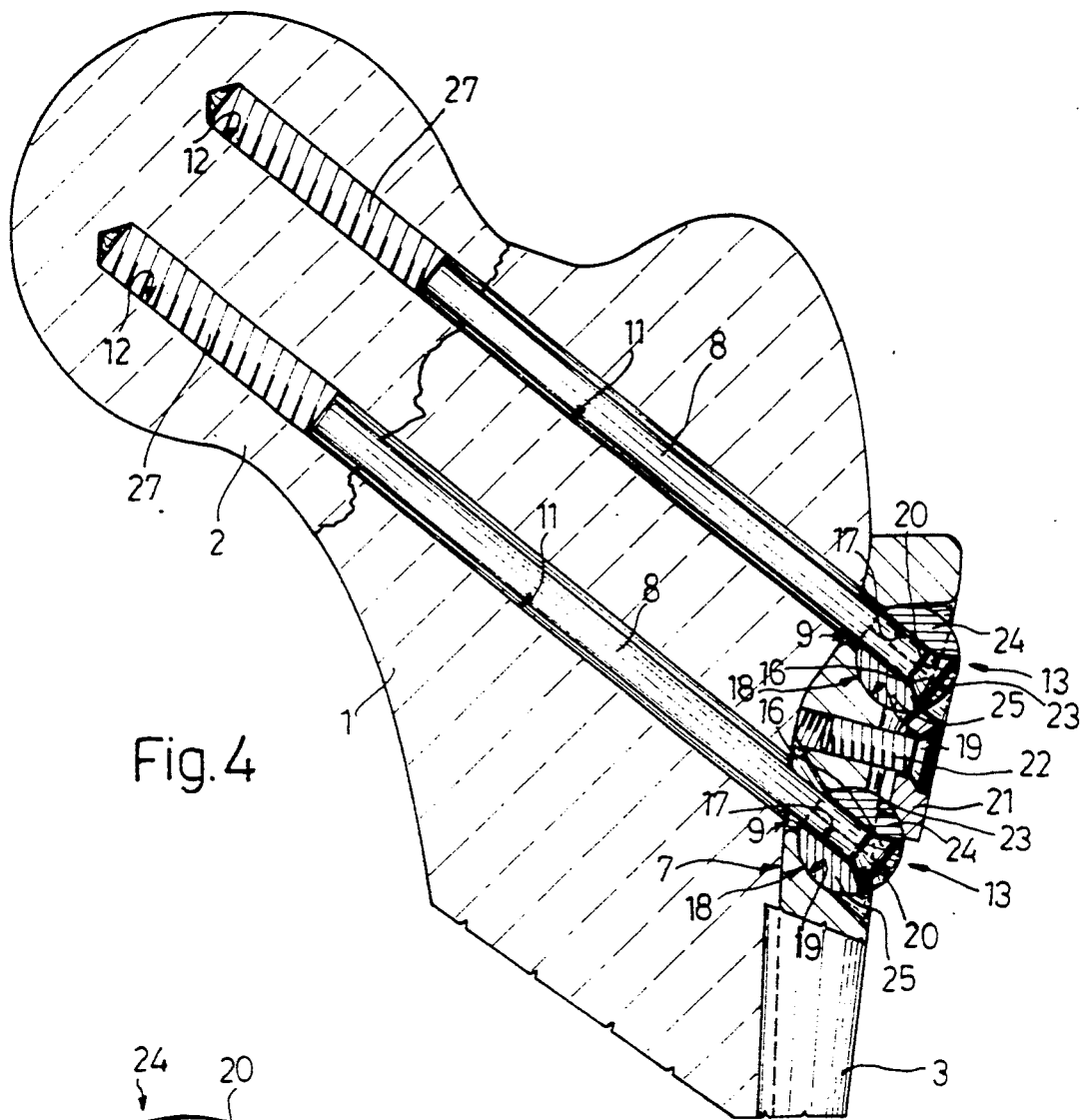
FIG. 4 shows a partially-sectioned side view of a second embodiment of the means according to the present invention.
Figure 5:
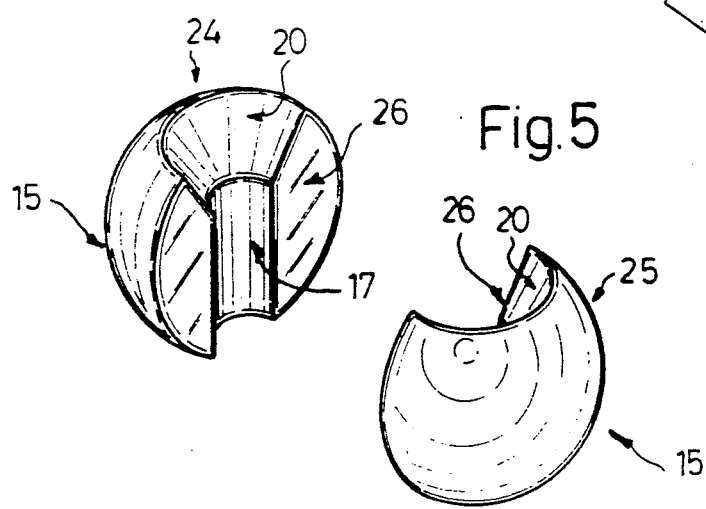
FIG. 5 shows a view in perspective of an adjustable element forming part of the FIG. 4 means.

Each of elements 15 may conveniently be formed as shown in FIGS. 4 and 5, in which case, it consists of two parts 24, 25 having flat mating surfaces 26 (FIG. 5) lying in the equatorial plane of the element. When each adjustable element 15 consists of a ball, therefore, parts 24 and 25 are separated by the equatorial plane of said ball.

The FIG. 4 embodiment may be employed when the threaded end portion 27 of each screw 8 presents a larger diameter than the screw shank. In this case, by virtue of the diameter of hole 17 in each adjustable element 15 being substantially equal to that of the screw shank, and therefore smaller than that of threaded portion 27, screw 8 may be removed from segments 1 and 2 by simply detaching parts 24 and 25 of each angle joint 13 from plate 3 as described later on.

Figure 7:
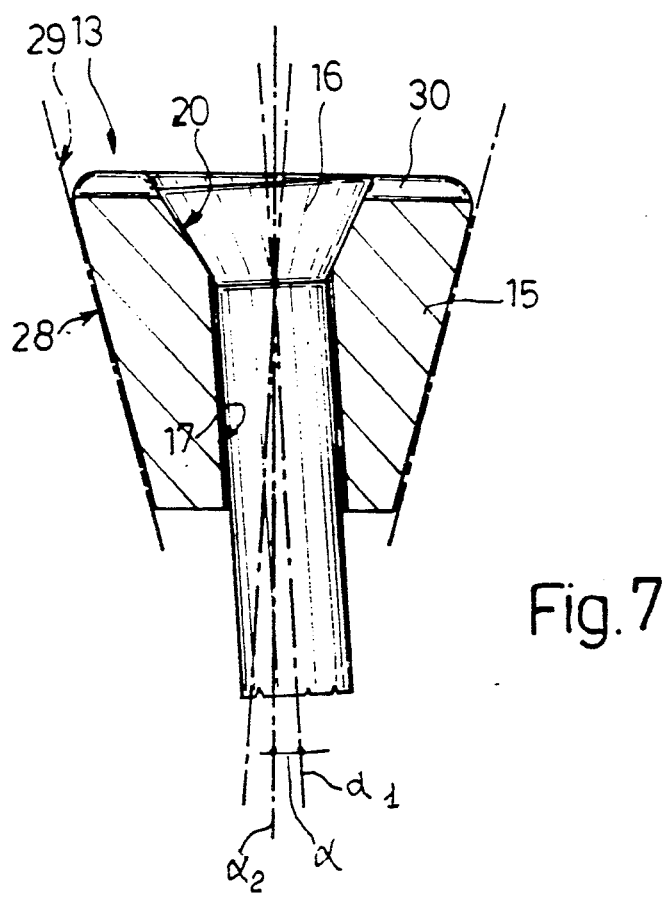
FIG. 7 shows a schematic section of two elements in FIG. 6.
Figure 3:
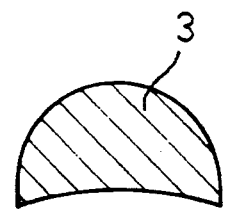
FIG. 3 shows a section along line III—III of the FIG. 2 means.

In the FIG. 6 embodiment, each angle joint 13 substantially comprises an adjustable element 15 having a hole 17 for the shank of screw 8, and at least a conical surface portion 28 cooperating with a conical seat 29 on plate 3, as shown clearly in FIG. 6. The axis (a1 in FIG. 7) of hole 17 in adjustable element 15 forms a predetermined angle a with axis a2 of conical surface portion 28.

The osteosynthesis means described above are employed as follows.

First of all, an assembly is formed comprising plate 3, adjustable elements 15, screws 8, plate 21 and screws 22 for connecting plate 21 and said elements to plate 3. Once holes 11 and 12 have been formed in bone segments 1 and 2, screws 8 are inserted inside holes 11 in segment 1 and screwed inside holes 12 in segment 2. Surface 7 of plate 3 is then placed on segment 1, as shown in FIG. 1, which operation is simplified by virtue of angle joints 13, which enable plate 3 to adjust in relation to screws 8, and so achieve perfect mating of surface 7 of plate 3 on segment 1 regardless of the position of the holes 11 and 12.

Plate 3 is then secured to segment 1 using screws 4 inserted inside holes 6.

The above procedure, therefore, not only provides for extremely straightforward connection of segments 1 and 2, but also for highly accurate mutual positioning of the same.

Moreover, the means according to the present invention provide for a high degree of versatility by enabling the connection of bone segments of different shapes and sizes, by virtue of angle joints 13 enabling adjustment of the axes of screws 8.

In addition to considerably improving the mechanical strength and stability of the connection, the means according to the present invention also provide for maintaining correct mutual positioning of the bone segments in the period immediately following surgery and pending complete knitting of the same, regardless of whether or not additional precautions are taken. In particular, when more than one screw 8 is employed, the resulting connection also presents a high mechanical resistance to the torques which would otherwise cause the bone segments to rotate about an axis parallel to that of the screws. During the period in which the fracture surfaces are absorbed, the contacting segments may undergo a change, particularly a reduction, in length, which changes are permitted by the special retaining conditions provided for by the means according to the present invention. Any reduction in length of the bone segments is permitted by virtue of the smooth shank portions of screws 8 sliding inside respective holes 11 in segment 1, and by virtue of heads 16 of screws 8 withdrawing from respective seats 20 on adjustable elements 15 and projecting in relation to plate 3 with no impairment in the characteristics of the connection. Moreover, once screws 8 are screwed inside holes 12 in segment 2, compressive stress may be produced as required between the mating surfaces of the fracture, for ensuring fast, safe knitting of the bone segments. Once the bone segments are knit strongly enough to dispense with screws 8, these are removed by simply unscrewing them. In the case of the FIG. 1 embodiment, the threaded portions of screws 8 may be withdrawn through holes 17 in adjustable elements 15. In the case of screws 8 of the FIG. 4 type, wherein threaded end portions 27 present a larger diameter than the screw shanks, screws 8 may be removed from the bone by detaching parts 24 and 25 of each adjustable element 15, the two-part design of which provides for detaching it easily from the rest of the assembly.

Once assembled as required, screws 8 may be locked in position by the locking means on the assembly, consisting of plates 21 and screws 22. By torquing screws 22, sufficient pressure is exerted by surface portions 23 of plates 21 on adjustable elements 15 for preventing any movement of the same.

As in the previous embodiment, angle joints 13 in the FIG. 6 embodiment enable the shank of each screw 8 to be positioned at any angle within a conical surface whose axis coincides with that of each hole 9. In fact, by virtue of the angle a formed between axes a1 and a2, rotation of adjustable element 15 inside respective conical seat 29 enables axis a1 of screw 8 to be positioned at a predetermined angle in relation to plate 3. For enabling rotation of adjustable element 15 as described, provision may be made on element 15 for a screwdriver slot 30.

To those skilled in the art it will be clear that changes may be made to both the form and arrangement of the component parts of the embodiments described and illustrated herein without, however, departing from the scope of the present invention.

We claim:

1. An osteosynthesis device for the connection of femur fracture segments, comprising:
   a support plate having a first surface adapted to contact the surface of one of the femur fracture segments and securable only thereto, a second opposite surface and at least two holes extending therethrough;

at least two screws, each insertable into a corresponding hole in said support plate and adapted to be inserted into corresponding holes in said segments, each said screw including a head and shank formed of a smooth portion and a threaded end portion, said threaded end portion having a length which is not greater than the length of a corresponding hole formed in another one of the femur fracture segments so as to be screwed only into the other one of the femur fracture segments, each one of said holes in said support plate being contoured by a spherical seat extending toward the second surface of said support plate;

an adjustable angle element associated with each of said holes in said support plate, each said adjustable angle element having an external spherical surface fitting into said spherical seat, a screw head seat for housing the head of one said screw and a diametrical hole engageable by the smooth portion of the respective screw to enable the axis of the screw to be positioned at any angle within a conical surface having an axis coinciding with an axis of the respective hole in the support plate;

a locking plate having a surface portion designed for engaging a corresponding surface portion of adjustable elements and leaving uncovered each said screw head seat; and connecting means for securing the locking plate to the support plate to cause the surface portion of the locking plate to exert a predetermined pressure on the adjustable elements for preventing movement of the adjustable elements in the spherical seats.

2. An osteosynthesis device for the connection of femur fracture segments, comprising:

a support plate having a first surface adapted to contact the surface of one of the femur fracture segments and securable only thereto, a second opposite surface and at least two holes extending therethrough;

at least two screws, each insertable into a corresponding hole on said support plate and adapted to be inserted into corresponding holes in said segments, each said screw including a head and a shank formed of a smooth portion and a threaded end portion, said threaded end portion having a length which is not greater than the length of a corresponding hole formed in another one of the femur fracture segments so as to be screwed only into the other one of the femur fracture segments, each one of said holes in said support plate being contoured by a spherical seat extending toward the second surface of said support plate;

an adjustable angle element associated with each of said holes in said support plate, each said adjustable angle element having an external spherical surface fitting into said spherical seat, a seat for housing the head of one said screw and a diametrical hole engageable by the smooth portion of the respective screw to enable the axis of the screw to be positioned at any angle within a conical surface having an axis coinciding with an axis of the respective hole in the support plate;

a locking plate having a surface portion for engaging the adjustable elements; and connecting means for securing the locking plate to the adjustable elements; and connecting means for securing the locking plate to the support plate to cause said surface portion of the locking plate to exert a predetermined pressure on the adjustable elements for preventing movement of the adjustable elements in the spherical seats;

wherein said threaded end of the shank of each said screw has a diameter greater than the diameter of the smooth portion thereof, and each said adjustable element is comprised of two parts having flat mating surfaces lying in an equatorial plane of the adjustable element, each said part being formed with an axial half of the diametrical hole of the adjustable element.

3. An osteosynthesis device for the connection of bone fracture segments, comprising:

a plate adapted to be secured to one of the bone fracture segments;

at least one screw for insertion into at least one corresponding hole in said plate and adapted to be screwed into corresponding holes in said segments, each said screw including a head and a shank formed of a smooth portion and a threaded end portion;

an angle joint located between each said screw and the respective hole in said plate for enabling the axis of said screw to be positioned in relation to said plate at any angle within a conical surface having an axis coinciding with an axis of the respective hole in the support plate, each said angle joint including an adjustable element having a hole for receiving the smooth portion of the shank of one said screw and at least a spherical surface portion;

said plate further including a spherical seat formed about each said hole in the plate for receiving the spherical surface portion of one said adjustable element and locking means for locking each said adjustable element and screw at a predetermined angle in relation to said plate, said locking means including a second plate and at least one threaded connecting means for securing said second plate to said first-mentioned plate, said second plate including a surface portion for engaging a portion of said adjustable element and leaving uncovered the head of said screw to exert a predetermined pressure on said adjustable element to prevent movement of the adjustable element in said spherical seat.

4. An osteosynthesis device according to claim 3, wherein the threaded end portion of each said screw has a length which is not greater than the length of a corresponding hole formed in one of said segments which is furthest from said first plate.

5. An osteosynthesis device according to claim 3, wherein each said adjustable element is comprised of a ball having said hole extending therethrough, said hole having an axis which passes through the center of the ball.

6. An osteosynthesis device according to claim 3, wherein each said adjustable element includes a seat for housing the head of a respective said screw, said second plate being designed as to leave uncovered said seat in said adjusting element.

7. An osteosynthesis device according to claim 6, wherein said plate includes two said spherical seats for receiving two said adjustable elements.

8. An osteosynthesis device according to claim 7, wherein said spherical seats are formed on an end portion of said plate.

9. An osteosynthesis device for the connection of bone fracture segments, comprising a plate adapted to be secured to one of the bone fracture segments;

at least one screw for insertion into at least one corresponding hole in said plate to be screwed into corresponding holes in said segments, each said screw including a head and a shank formed of a smooth portion and a threaded end portion;

and angle joint located between each said screw and the respective hole in said plate for enabling the axis of said screw to be positioned in relation to said plate at any angle within a conical surface having an axis coincident with an axis of the respective hole in the support plate, each said joint including an adjustable element having a hole for receiving the smooth portion of the shank of one said screw and at least a spherical surface portion; and said plate further including a spherical seal formed about each said hole in the plate for receiving the spherical surface potion of one said adjustable element;

wherein each said adjustable element is comprised of two parts having flat mating surfaces lying in an equatorial plane of the adjustable element.

10. An osteosynthesis device for the connection of bone fracture segments, comprising:

a plate adapted to be secured to one of the bone fracture segments;

at least one screw for insertion into at least one corresponding hole in said plate and adapted to be screwed into corresponding holes in said segments, each said screw including a head and a shank formed of a smooth portion and a threaded end portion;

an angle joint located between each said screw and the respective hole in said plate for enabling the axis of said screw to be positioned in relation to said plate an any angle within a conical surface having an axis coinciding with an axis of the respective hole in the support plate, each said angle joint including an adjustable element having a hole for receiving the smooth portion of the shank of one said screw, and at least a conical surface portion, with the hole in the adjustable element forming a predetermined angle with the axis of the conical surface portion of the adjustable element; and said plate further including a conical seat formed about each said hole in the plate for receiving the conical surface portion of one said adjustable element.

11. An osteosynthesis device according to claim 10, wherein each said adjustable element is provided with a seat housing said head.

12. An osteosynthesis device for the connection of femur fracture segments, comprising:

a support plate having a first surface adapted to contact the surface of one of the femur fracture segments and securable only thereto, a second opposite surface and at least two holes extending therethrough;

at least two screws, each insertable into a corresponding hole in said support plate and adapted to be inserted into corresponding holes in said segments, each said screw including a head and a shank formed of a smooth portion and a threaded end portion, said threaded end portion having a pg,24 length which is not greater than the length of a corresponding hole formed in another one of the femur fracture segments so as to be screwed only into the other one of the femur fracture segments, each one of said holes in said support plate being contoured by a conical seat extending toward the second surface of said support plate; and an adjustable angle element associated with each of said holes in said support plate, each said adjustable angle element having a external conical surface fitting into said conical seat, a seat for housing the head of one said screw and a diametrical cylindrical hole engageable by the smooth portion of the respective screw to enable the axis of the screw to be positioned at any angle within a conical surface having an axis coinciding with an axis of the respective hole in the support plate.

* * * * *